United States Patent [19]

Nieminen

[11] 4,329,587
[45] May 11, 1982

[54] DEVICE FOR SUPPORTING PATIENT IN PANORAMIC X-RAY RADIOGRAPHY

[75] Inventor: Timo Nieminen, Helsinki, Finland

[73] Assignee: Syntex (U.S.A.) Inc., Palo Alto, Calif.

[21] Appl. No.: 118,378

[22] Filed: Feb. 5, 1980

Related U.S. Application Data

[63] Continuation of Ser. No. 940,701, Sep. 8, 1978, abandoned.

[30] Foreign Application Priority Data

Oct. 24, 1977 [FI] Finland .................................. 773160

[51] Int. Cl.³ ............................................. G03B 41/16
[52] U.S. Cl. ................................................. 250/439 P
[58] Field of Search ..................................... 250/439 P

[56] References Cited

U.S. PATENT DOCUMENTS

| 3,673,408 | 6/1972 | Moss | 250/439 P |
| 3,743,832 | 7/1973 | Wright | 250/439 P |
| 4,002,915 | 1/1977 | Weiss | 250/439 P |

*Primary Examiner*—Craig E. Church
*Attorney, Agent, or Firm*—John A. Dhuey; Joseph I. Hirsch

[57] ABSTRACT

The invention at hand concerns a device for supporting the patient in panoramic X-ray radiography. The device has a certain head supporting equipment to support the patient's head in order to keep it in a fixed position during the X-ray radiography. The device also has equipment for placing the patient's head in the right position for radiography. These make it possible to move the X-ray machine in relation to the head supporting equipment, so that the patient's head can be placed in the appropriate position in relation to the X-ray machine.

3 Claims, 1 Drawing Figure

U.S. Patent
May 11, 1982
4,329,587
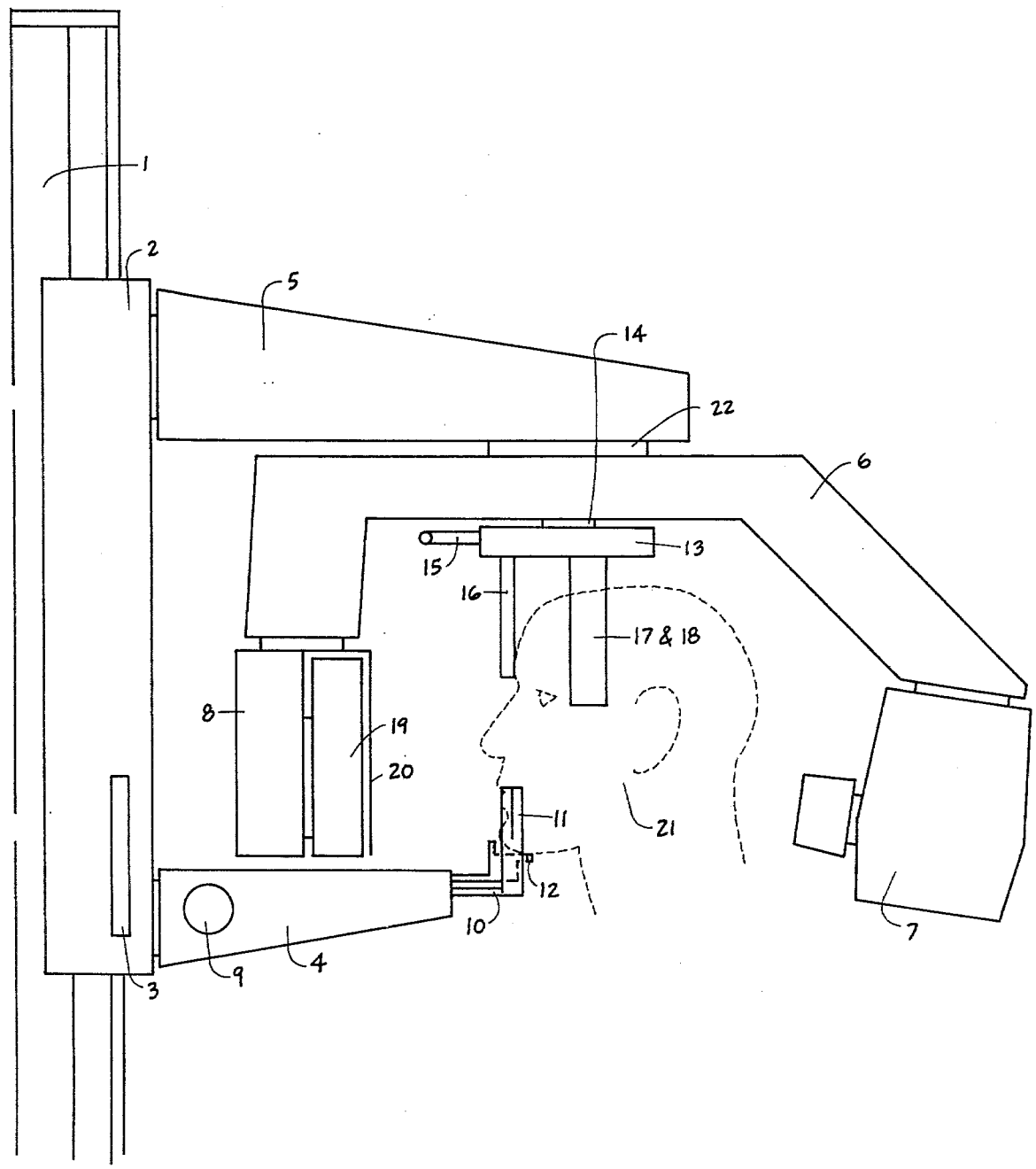

DEVICE FOR SUPPORTING PATIENT IN PANORAMIC X-RAY RADIOGRAPHY

This is a continuation of application Ser. No. 940,701, filed Sept. 8, 1978, now abandoned.

BACKGROUND OF THE INVENTION

In the panoramic tomographic radiography technique, a layer of certain thickness of the object is visible on the film. This is the so-called picture layer, the form, location and thickness of which can be affected through appropriate planning of the geometry pertaining to the projection of the object. Normally, in this photo technique, the radiation source and the film move in relation to the patient, who thus remains still during the radiographing. The desired point of the object is pictured accurately on the film, if the same speed is chosen for the film and the projection point on the surface of the film of the point to be pictured.

In the presently existing arrangements the layer to be pictured, without exception, is kept steady and the patient's head is moved with the help of head supports, so that the patient's head can be set in the right position in relation to the layer to be pictured.

In panoramic tomographic radiography, the position of the patient in relation to the layer to be pictured is a delicate operation in terms of the final outcome. Even the smallest mistake when positioning the patient will show in the X-ray picture. The weakness of known systems is the fact, that the patient's head has to be positioned correctly and at the same time supported properly during radiography.

The following U.S. patents will give more information about the present level of the technology: U.S. Pat. Nos. 2,684,446; 2,798,958; 3,045,118; 3,521,057; 3,356,913 and 3,636,349.

SUMMARY OF THE INVENTION

The purpose of the invention was to develop as simple and clear a supporting device as possible. In practice, it was a major importance that the supporting and positioning of the patient in relation to the layer to be pictured be as easy as possible. The placing of the patient's head in relation to the layer to be pictured had to be easily checked.

The essence of the invention is that the layer to be pictured can be moved to its proper place in relation to the patient after the patient has already been placed correctly with the aid of the supporting equipment.

The separating of the support of the patient's head on the one hand and on the other hand the position of the picture layer in relation to the patient considerably facilitates the practical procedures for handling the patient, which, of course, is the most critical phase for achieving a good final result.

DESCRIPTION OF THE DRAWING

FIG. 1 presents schematically the profile of the invented device for supporting the patient's head in a certain performance in the panoramic X-ray machine.

DETAILED DESCRIPTION OF THE INVENTION

Solid base 1 is the base of the whole X-ray machine. Base 2, mounted in bearings, moves vertically in relation to base 1. Part 3 is a lever, with which the balanced moving base 2 can be moved vertically. Parts 4 and 5 are attached to part 2. Supporting column 6 is suspended rotatingly in relation to part 5. Radiation source 7 and cassette holder 8 are attached to supporting column 6. By turning knob 9, sliding piece 10 can be moved linearly in relation to part 4. Indicator 11 is attached to sliding piece 10. Indicator 11 shows the position of the layer to be pictured in relation to the patient 21. The suspension point 22 of supporting column 6 is mechanically attached to sliding piece 10, so that it (22) moves in the same direction as sliding piece 10 when turning knob 9.

Chin support 12 is detachably attached to part 4. Base 13 of the head support is stationarily attached to part 5 through attaching piece 14. Forehead support 16 and temporal supports 17 and 18 support the patient's head 21 from above while chin support 12 supports the patient's chin. Locking lever 15 can lock temporal supports 17 and 18 for a more efficient support of the patient. There is a mechanical transmission between forehead support 16 and temporal supports 17 and 18, so that when the patient pushes forehead support 16 forward, temporal supports 17 and 18 are pressed symmetrically from both sides against the patient's head 21.

Cassette cart 19 moves during the projection with changing speed linearly in relation to cassette holder 8. Cassette cart 18 contains the film cassette, where the X-ray film is located. The beam of X-rays coming from tube end 7 reaches the film in cassette cart 19 through the patient's head 21 through an opening in secondary shutter 20.

Characteristic for the invention is the very basic observation that by moving suspension point 22 of supporting column 6 in relation to the patient, the picture layer which is projected accurately as determined by the movement of supporting column 6 can be moved in relation to the patient. To make this move possible, the X-ray machine must be planned so that column 6 is suspended only through one part 22 and base 13 of the head support attached through attaching piece 14, which can move freely through suspension point 22. Attaching piece 14 is completely stationary in relation to part 5 while suspension point 22 gets to move linearly in relation to part 5. Furthermore, sliding piece 10, to which indicator 11 is attached, is mechanically coupled to suspension point 22 so that they move the same distance parallelly when knob 9 is turned.

I claim:
1. A device for supporting a patient during panoramic X-ray radiography comprising:
(a) support structure;
(b) a radiation source;
(c) a film holder, said radiation source and said film holder being mounted on said supporting structure on opposite sides of a patient to be radiographed when situated therebetween;
(d) a base having a pair of vertically spaced, horizontally extending arms;
(e) means fixedly secured to the upper arm of said base for supporting the upper portion of the head of a patient;
(f) means movably suspending said supporting structure from the upper arm of said base for rotational and horizontal linear movement relative to said base and the upper arm;
(g) indicator means supported on the lower arm of said base and adapted for horizontal linear movement relative to the lower arm and said base and the patient for indicating the position of the layer to be radiographed in relation to the patient; and (h) means coupling said indicator means and said movable suspension means for horizontally, linearly moving said movable suspension means in unison with said indicator means.

2. The device of claim 1 including a slide member movably supported on the lower arm of said base member for linear movement with said suspension means and supporting said indicator means for indicating the linearly moved position of said suspension means relative to the patient.

3. The device of claim 1 or 2 wherein said suspension means moves linearly in the direction of the axis of symmetry of the dental arch of a patient.

* * * * *